United States Patent
Dekel et al.

(10) Patent No.: US 10,410,363 B2
(45) Date of Patent: Sep. 10, 2019

(54) JAW SURFACE BASED REGISTRATION

(71) Applicant: Claronav Inc., North York (CA)

(72) Inventors: Doron Dekel, Toronto (CA); Arish Qazi, Oakville (CA)

(73) Assignee: CLARONAV INC., North York (CA)

( * ) Notice: Subject to any disclaimer, the term of this patent is extended or adjusted under 35 U.S.C. 154(b) by 0 days.

(21) Appl. No.: 16/037,517

(22) Filed: Jul. 17, 2018

(65) Prior Publication Data

US 2019/0026910 A1    Jan. 24, 2019

Related U.S. Application Data

(60) Provisional application No. 62/533,905, filed on Jul. 18, 2017.

(51) Int. Cl.
*G06T 7/33* (2017.01)
*A61B 6/14* (2006.01)
(Continued)

(52) U.S. Cl.
CPC ............ *G06T 7/337* (2017.01); *A61B 6/14* (2013.01); *A61B 6/5247* (2013.01); *A61C 9/008* (2013.01);
(Continued)

(58) Field of Classification Search
CPC ....... G06T 7/0012; G06T 7/0014; G06T 7/13; G06T 7/30; G06T 7/33; G06T 7/337;
(Continued)

(56) References Cited

U.S. PATENT DOCUMENTS

| | | | |
|---|---|---|---|
| 9,125,624 B2 | 9/2015 | Dekel et al. | A61B 6/583 |
| 9,402,691 B2 | 8/2016 | Merritt et al. | A61B 19/54 |

(Continued)

FOREIGN PATENT DOCUMENTS

| | | | |
|---|---|---|---|
| EP | 3094255 | 7/2015 | A61B 6/00 |
| WO | 2008083874 A2 | 7/2008 | A61B 6/14 |

(Continued)

OTHER PUBLICATIONS

Etienne et al.., "A new approach for dental implant aided surgery. A pilot evaluation.", CARS 2000, pp. 927-931.

(Continued)

*Primary Examiner* — Andrew W Johns
(74) *Attorney, Agent, or Firm* — Bereskin & Parr LLP/S.E.N.C.R.L., s.r.l.

(57) ABSTRACT

A computer-implemented method and system are provided for registering a human jaw with a volumetric computed tomography image of that jaw positioned in an image reference coordinate system and stored in a computer-readable memory. The method involves attaching a jaw marker to the jaw to establish a pose trackable jaw reference coordinate system; moving a surface sampling tool over at least one portion of the surface of the jaw while operating a pose tracking system and a computer processor to record samples in the jaw reference coordinate system indicative of locations within the at least one portion of the surface of the jaw; operating a computer processor to determine an approximate initial registration mapping; then beginning with the approximate initial registration mapping, incrementally adjust the registration mapping. Incrementally adjusting the registration mapping involves computing an edge proximity value at each sample location mapped to the image by the registration mapping.

29 Claims, 9 Drawing Sheets

(51) Int. Cl.
  *G06T 7/73* (2017.01)
  *G06T 7/13* (2017.01)
  *A61B 6/00* (2006.01)
  *A61C 9/00* (2006.01)
  *G06T 7/00* (2017.01)

(52) U.S. Cl.
  CPC .......... *A61C 9/0053* (2013.01); *G06T 7/0014* (2013.01); *G06T 7/13* (2017.01); *G06T 7/74* (2017.01); *G06T 2207/10081* (2013.01); *G06T 2207/20221* (2013.01); *G06T 2207/30036* (2013.01); *G06T 2207/30204* (2013.01)

(58) Field of Classification Search
  CPC ........ G06T 2207/30036; A61C 9/0053; A61C 9/008; A61B 5/0059; A61B 5/0064; A61B 6/14; A61B 6/5229; A61B 6/5247
  See application file for complete search history.

(56) References Cited

U.S. PATENT DOCUMENTS

| | | | |
|---|---|---|---|
| 2010/0124367 A1* | 5/2010 | Cizek | G06T 7/33 382/132 |
| 2017/0290554 A1 | 10/2017 | Merritt | A61B 6/12 |

FOREIGN PATENT DOCUMENTS

| | | |
|---|---|---|
| WO | 2012068679 A1 | 5/2012 |
| WO | 2016090476 A1 | 6/2016 |

OTHER PUBLICATIONS

Medtronic Neurosurgery, "StealthStation EM Navigation Patient Registration", YouTube Video, Apr. 30, 2014.
Scopis Surgical Navigation, "Scopis Surgical Navigation: Image to Patient Registration", YouTube Video. Nov. 27, 2012.
Yaniv, "Rigid Registration", Image Guided Interventions, 2007.
Granger et al., "Rigid Point-Surface Registration using Oriented Points and an EM Variant of ICP for Computer Guided Oral Implantology", Institut National de Recherche en Informatique et en Automatique, 2006.
Granger et al., "Multi-scale EM-ICP: A Fast and Robust Approach for Surface Registration", Institut National de Recherche en Informatique et en Automatique, 2002, pp. 418-432.
Flugge, et al., "Registration of cone beam computed tomography data and intraoral surface scans—A prerequisite for guided implant surgery with CAD/CAM drilling guides", Clin. Oral Impl. Res. 28, 2017, pp. 1113-1118.
Horn, "Closed-form solution of absolute orientation using unit quaternions", Journal of the Optical Society of America A., vol. 4, pp. 629-642, Apr. 1987.

* cited by examiner

JAW SURFACE BASED REGISTRATION

PRIORITY

This application claims the benefit of U.S. Provisional Patent Application No. 62/533,905, filed Jul. 18, 2017, which is incorporated herein by reference in its entirety.

FIELD

The described embodiments relate to the field of medicine, in particular, the field of dental navigation systems.

BACKGROUND

Dental navigation systems are increasingly common and commercially available. Many existing dental navigation systems, such as that described in U.S. Pat. No. 9,125,624 and U.S. Pat. No. 9,402,691 involve a three-dimensional (3D) coordinate mapping between locations in a subject jaw, that is, the patient's jaw that is being optically tracked, and homologous locations in a pre-acquired volumetric computed tomography (CT) image of that subject jaw.

The parameters of the 3D coordinate mapping are commonly in the form of a matrix, representing a rigid 3D coordinate transform (the "registration mapping") between a reference coordinate space associated with the subject jaw and a reference coordinate space associated with the CT image. The matrix can be computed using an algorithmic process called registration.

Existing methods for registering a rigid object, such as a human jaw, are generally based on some combination of points-points, points-surface and surface-surface alignment. The use of fiducials (i.e., an artificial object of known geometry with boundaries that can be reliably detected in the image) enables a high degree of registration reliability and accuracy, but incurs an undesirable time and cost overhead.

Some prior art publications describe a fiducial-free registration of a jaw with its image. For example, U.S. Patent Publication No. 2017/0290554 discloses a system that initially aligns landmark trace points to the surface of the teeth and then uses an iterative closest point (ICP) algorithm to refine the alignment between trace points and the surface of the teeth. The surface geometry is extracted from the CT image using an iso-surface following algorithm (i.e., "marching cubes") and the points are collected using a position-tracked calibrated probe with a spherical tip. Following a probe tip calibration and the attachment of a trackable thermoplastic fixture to the teeth as a reference, a point-to-point registration is used to provide an initial approximate alignment of the jaw with the CT image. In a subsequent refinement step, an operator performs a long trace over the surface of the teeth and the computer iteratively adjusts the registration mapping to reduce the average distance between the trace and the previously extracted iso-surface.

Existing dental navigation systems and methods referenced above work reasonably well on models, but frequently fail when applied to patient jaws because the surface geometry obtained by iso-surface segmentation, or other automated segmentation algorithm applied to the commonly used cone-beam CT (CBCT) images, can be highly unreliable and distorted due to a variety of reasons. First, non-uniformities in the intensities can be present across the imaged field. Second, streak artifacts are often present near high-density regions of the CT image. As well, non-uniformities due to varying teeth density or artificial materials introduced to the mouth from previous dental treatments can also cause distortions. Furthermore, since the time delay between from the CT scan to the surgery can be several months, teeth movement can occur within this time to render some portions the CT image an unreliable depiction of the jaw surface during surgery. Finally, movement of the patients' jaw during scanning can also cause geometrical distortions in the CT image.

Another major challenge with existing dental navigation systems and methods is the attachment of the fiducial to the jaw, which typically covers three or more teeth. Coverage of three or more teeth substantially reduces the exposed teeth surfaces available for the registration of the alignment of the jaw with the CT image.

SUMMARY

The various embodiments described herein generally relate to methods (and associated systems configured to implement the methods) for registering a human jaw with a volumetric computed tomography image of that jaw positioned in an image reference coordinate system and stored in a computer-readable memory.

An example method involves rigidly attaching a pose trackable jaw marker to the jaw, or to a structure in a rigid geometrical relationship to the jaw, to establish a pose trackable jaw reference coordinate system; moving a pose trackable surface sampling tool over at least one portion of the surface of the jaw while operating a pose tracking system and a computer processor to record samples in the jaw reference coordinate system indicative of locations within the at least one portion of the surface of the jaw; operating a computer processor to determine an approximate initial registration mapping; then beginning with the approximate initial registration mapping, operating the computer processor to incrementally adjust the registration mapping. Incrementally adjusting the registration mapping involves: i) mapping the samples to the image reference coordinate system using the registration mapping to provide mapped sample locations, ii) for each mapped sample location, computing an edge proximity value based on an analysis of image values at a plurality of image locations derived from the mapped sample location, and iii) adjusting the registration mapping based on the edge proximity values at the mapped sample locations.

In some embodiments, computing the edge proximity value can involve computing image gradients at the plurality of image locations.

In some embodiments, computing the edge proximity value can involve analyzing image values at a plurality of image locations derived from the mapped sample location to select an image location and computing a distance from the selected image location to another location derived from the mapped sample location.

In some embodiments, the pose trackable surface sampling tool can be an intraoral scanner.

In some embodiments, the pose trackable surface sampling tool can be a pose trackable tracer tool with a tracer tip of known shape, and moving a surface sampling tool can involve dragging the tracer tip over at least one portion of the surface of the jaw such that the tracer tip contacts the surface of the jaw.

In some embodiments, the method can further involve marking at least one corresponding location in both the image reference coordinate system and the jaw reference coordinate system. Determining an approximate initial registration mapping can involve: computing an initial rotation mapping based on estimating the orientation of the jaw in the jaw reference coordinate system based on a known orientation of the jaw relative to the jaw marker; and computing the initial registration mapping based on the initial rotation mapping and the at least one corresponding location.

In some embodiments, when the pose trackable surface sampling tool is an intraoral scanner, the method can further involve marking on the image at least one landmark location on the jaw surface. As well, the intraoral scanner can be positioned such that a known location within a capture region of the intraoral scanner corresponds approximately to a landmark location marked on the image and a sample location at the known location within the capture region can be obtained. Determining an approximate initial registration mapping can be based at least in part on the correspondence between the at least one landmark location marked on the image and the sample location at the known location within the capture region.

In some embodiments, the method can further involve marking on the image at least one landmark location on the jaw surface. As well, moving the pose trackable surface sampling tool over at least one portion of the surface of the jaw can start at a location corresponding to a landmark location marked on the image and determining an approximate initial registration mapping can be based at least in part on the correspondence between the at least one landmark location marked on the image and a sample location recorded at the start of moving the pose trackable surface sampling tool.

In some embodiments, the method can further involve marking on the image at least one landmark location on the jaw surface. As well, moving the pose trackable surface sampling tool over at least a portion of the surface of the jaw can end at a location corresponding to a landmark location marked on the image and determining an approximate initial registration mapping can be based at least in part on the correspondence between the at least one landmark location marked on the image and a sample location recorded at the end of moving the pose trackable surface sampling tool.

In some embodiments, the landmark location can be marked on a rendering of the jaw surface, which is mathematically flattened along a ridge curve of the jaw.

In some embodiments, moving the pose trackable surface sampling tool over at least one portion of the surface of the jaw can involve moving the pose trackable surface sampling tool over at least three portions of the surface of the jaw such that the samples include at least three subsets of samples, each subset of samples being from a different portion of the surface of the jaw in the at least three portions of the surface of the jaw.

In some embodiments, operating the computer processor to incrementally adjust the registration mapping can further involve, for each subset of samples: operating the computer processor to perform step i) to step iii) for that subset of samples to adjust the registration mapping to determine a trace-specific adjusted registration mapping; operating the computer processor to perform step i) to step iii) for all of the remaining subsets of samples to adjust the registration mapping to determine a complementary adjusted registration mapping; and determining a difference between the trace-specific adjusted registration mapping and the complementary adjusted registration mapping, and, when that difference exceeds a maximum threshold, then further operating the computer processor to send a notification identifying that subset of samples.

In some embodiments, when the pose trackable surface sampling tool is a pose trackable surface sampling tool, the method can further involve after determining a final registration, performing a visual registration accuracy check. The accuracy check can involve: placing the tracer tip in contact with a jaw surface location; mapping the tracer tip to the image reference coordinate system using the registration mapping; selecting an image location likely to correspond to the jaw surface location nearest to the mapped tracer tip surface based on analyzing image values at a plurality of image locations derived from the mapped surface of the tracer tip; and displaying an image illustrating the gap between the selected image location and the mapped tracer tip surface location closest to the selected image location.

In some embodiments, when the pose trackable surface sampling tool is a pose trackable surface sampling tool, the tracer tip shape can be substantially spherical, and selecting the plurality of image locations in the computation of the edge proximity value in step ii) of adjusting the registration mapping can involve defining a plurality of vectors emanating in different directions from the mapped center of the tracer tip and selecting locations along each such vector.

An example system includes a pose trackable jaw marker that is rigidly attachable to the jaw or to a structure in a rigid geometrical relationship to the jaw to establish a pose trackable jaw reference coordinate system; a pose tracker for tracking poses of the pose trackable jaw marker and a pose trackable surface sampling tool; a computer-readable memory for storing the volumetric computed image; and a computer processor. The computer processor is operatively coupled to the computer-readable memory and the pose tracker. The computer processor is configured for: recording samples in the jaw reference coordinate system indicative of locations within the at least one portion of the surface of the jaw while the pose trackable surface sampling tool is moved over at least one portion of the surface of the jaw; determining an approximate initial registration mapping; then beginning with the approximate initial registration mapping, incrementally adjusting the registration mapping. The computer processor being configured to incrementally adjust the registration can include the computer processor being configured to: i) map the samples to the image reference coordinate system using the registration mapping to provide mapped sample locations, ii) for each mapped sample, compute an edge proximity value based on an analysis of image values at a plurality of image locations derived from the mapped sample location, and iii) adjust the registration mapping based on the edge proximity values at the mapped sample locations.

In some embodiments, the computer processor configured for computing the edge proximity value can include the computer processor being configured for computing image gradients at the plurality of image locations.

In some embodiments, the computer processor being configured for computing the edge proximity value can include the computer processor being configured for analyzing image values at a plurality of image locations derived from the mapped sample location to select an image location and computing a distance from the selected image location to another image location derived from the mapped sample location.

In some embodiments, the system can further include the pose trackable surface sampling tool.

In some embodiments, the pose trackable surface sampling tool can include an intraoral scanner.

In some embodiments, the pose trackable surface sampling tool can include a pose trackable tracer tool with a tracer tip of known shape for contacting the surface of the jaw as the pose trackable surface sampling tool is moved; and the computer-readable memory further stores the shape of the tracer tip.

In some embodiments, the computer processor can be further configured for receiving at least one corresponding location in both the image reference coordinate system and jaw reference coordinate system; and the computer processor being configured for determining an approximate initial registration mapping can include the computer processor being configured for: computing an initial rotation mapping based on estimating the orientation of the jaw in the jaw reference coordinate system based on a known orientation of the jaw relative to the jaw marker; and computing the initial registration mapping based on the initial rotation mapping and the at least one corresponding location.

In some embodiments, when the pose trackable surface sampling tool includes an intraoral scanner, the computer processor can be further configured for: receiving at least one landmark location on the jaw surface on the image; receiving a sample location at a known location within a capture region of the intraoral scanner when the intraoral scanner is positioned with the known location within the capture region at approximately a landmark location marked on the image; and determining an approximate initial registration mapping based at least in part on the correspondence between the at least one landmark location marked on the image and the sample location at the known location within the capture region.

In some embodiments, the computer processor can be further configured for: receiving at least one landmark location on the jaw surface on the image; receiving a sample location when the pose trackable surface sampling tool starts to be moved over at least one portion of the surface of the jaw at a location corresponding to a landmark location marked on the image; and determining an approximate initial registration mapping based at least in part on the correspondence between the at least one landmark location marked on the image and a sample location recorded at the start of moving the pose trackable surface sampling tool.

In some embodiments, the computer processor is further configured for: receiving at least one landmark location on the jaw surface on the image; receiving a sample location when the pose trackable surface sampling tool stops being moved over at least one portion of the surface of the jaw at a location corresponding to a landmark location marked on the image; and determining an approximate initial registration mapping based at least in part on the correspondence between the at least one landmark location marked on the image and a sample location recorded at the end of moving the pose trackable surface sampling tool.

In some embodiments, the landmark location can be marked on a rendering of the jaw surface which is mathematically flattened along a ridge curve of the jaw.

In some embodiments, the computer processor being configured for recording samples in the jaw reference coordinate system indicative of locations within the at least one portion of the surface of the jaw while the pose trackable surface sampling tool is moved over at least one portion of the surface of the jaw can include the computer processor being configured for recording samples in the jaw reference coordinate system indicative of at least three portions of the surface of the jaw such that the samples comprise at least three subsets of samples, each subset of samples being from a different portion of the surface of the jaw in the at least three portions of the surface of the jaw.

In some embodiments, the computer processor being configured for incrementally adjusting the registration mapping can further involve, for each subset of samples: performing step i) to step iii) for that subset of samples to adjust the registration mapping to determine a trace-specific adjusted registration mapping; performing step i) to step iii) for all of the remaining subsets of samples to adjust the registration mapping to determine a complementary adjusted registration mapping; and determining a difference between the trace-specific adjusted registration mapping and the complementary adjusted registration mapping, and, when that difference exceeds a maximum threshold, then further the computer processor being further configured for sending a notification identifying that subset of samples.

In some embodiments, when the pose trackable surface sampling tool includes a pose trackable tracer tool, the system can further include the computer processor being configured for after determining a final registration, performing a visual registration accuracy check. The accuracy check can include receiving a tracer tip when the tracer tip is in contact with a jaw surface location; mapping the tracer tip to the image reference coordinate system using the registration mapping; selecting an image location likely to correspond to the jaw surface location nearest to the mapped tracer tip surface based on analyzing image values at a plurality of image locations derived from the mapped surface of the tracer tip; and displaying an image illustrating the gap between the selected image location and the mapped tracer tip surface location closest to the selected image location.

In some embodiments, when the pose trackable surface sampling tool includes a pose trackable tracer tool, the shape of the tracer tip can be substantially spherical, and the computer processing being configured for selecting the plurality of image locations in the computation of the edge proximity value in step ii) of adjusting the registration mapping can include the computer processing being configured for defining a plurality of vectors emanating in different directions from the mapped center of the tracer tip and selecting locations along each such vector.

BRIEF DESCRIPTION OF THE DRAWINGS

Several embodiments will now be described in detail with reference to the drawings, in which.

Figure 1:
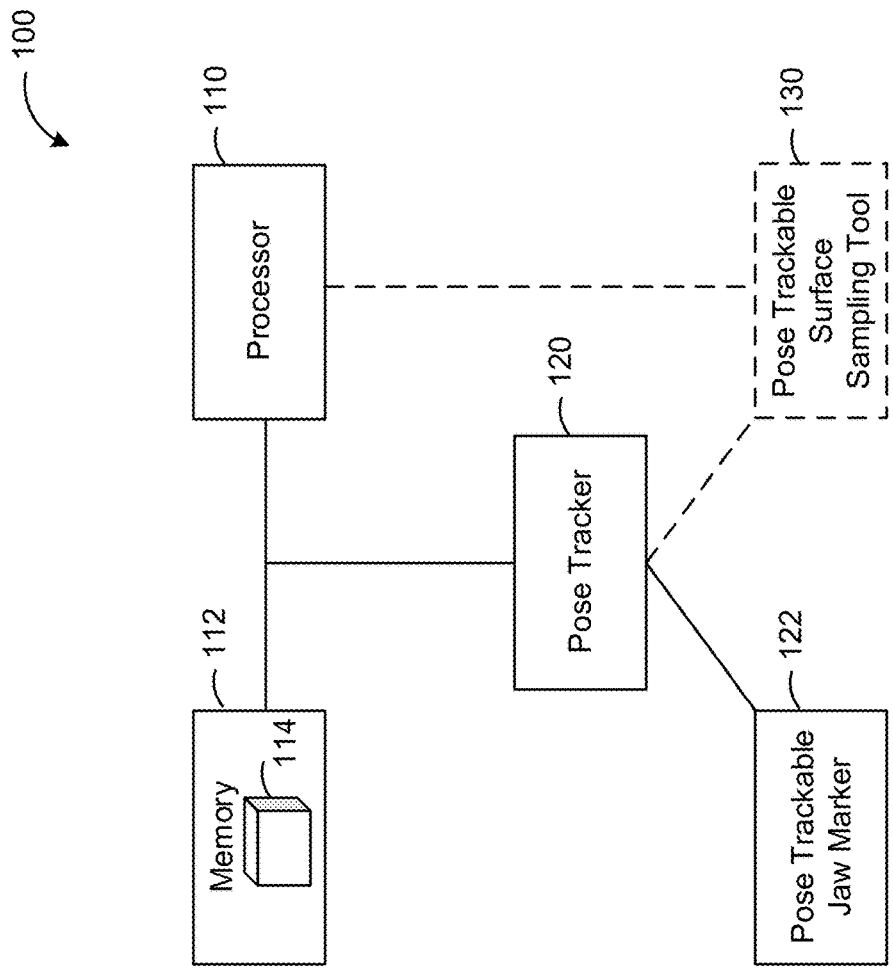
FIG. 1 is a block diagram of a system for registering a human jaw with a volumetric computed tomography image of that jaw positioned in an image reference coordinate system.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In embodiments, aspects of methods described herein, such as method 400 described with reference to FIGS. 4A and 4B below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication component. For example and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication component may be a network communication interface. In embodiments in which elements are combined, the communication component may be a software communication interface, such as those for inter-process communication (IPC). In still other embodiments, there may be a combination of communication components implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

The subject matter of the present application can enable a dental navigation system to obtain a registration mapping between a jaw reference coordinate system (hereinafter "RCS") and an image RCS. It should be noted that the term "RCS" relates to a three-dimensional (3D) coordinate system used in referencing locations on or inside an object of interest with which the RCS is associated. For example, a jaw RCS relates to an RCS associated with an actual jawbone that will be the subject of a dental procedure. An image RCS relates to an RCS associated with a computed tomography (CT) volumetric (3D) image of the actual jawbone that will be the subject of a dental procedure. The image RCS can provide accuracy in the order of less than a millimeter, within the region in which the dental procedure takes place. Dental procedures can include drilling or cutting the jawbone, teeth, mucosa, or other structures anchored to the jaw bone, which herein are considered an integral part of the jaw.

It should be noted that the term "registration mapping" relates to a coordinate mapping between two RCSs. A registration mapping closely aligns corresponding locations in the two RCSs. The term "rigid registration mapping" relates to registration mapping with only six degrees of freedom (DOF), namely three degrees of freedom for 3D translation and three degrees of freedom for 3D rotation. "Rigid registration mapping" does not correct for scaling or warping of an object's appearance in the two RCSs.

Reference is first made to FIG. 1, which is a block diagram of a dental navigation system 100. As shown in FIG. 1, the dental navigation system 100 includes a processor 110 operatively coupled to a memory 112 and a pose tracker 120. In some embodiments, each of the processor 110 and the memory 112 may be combined into a fewer number of components or may be separated into further components. Although only one pose tracker 120 is shown in FIG. 1, the dental navigation system 100 can include more pose trackers 120. The system 100 may be distributed over a wide geographic area and the processor 110 can communicate with the memory 112 and the pose tracker 120 via a network (not shown). The system 100 can include any appropriate communication component (not shown) to provide access to the network or enable communication between devices and systems.

The processor 110 may be any suitable processors, controllers, digital signal processors, graphics processing units, application specific integrated circuits (ASICs), and/or field programmable gate arrays (FPGAs) that can provide sufficient processing power depending on the configuration, purposes and requirements of the system 100. In some embodiments, the processor 102 can include more than one processor with each processor being configured to perform different dedicated tasks.

The processor 110 may be configured to control the operation of the system 100. The processor 110 can include modules that initiate and manage the operations of the dental navigation system 100. The processor 110 may also determine, based on received data, stored data and/or user preferences, how the dental navigation system 100 may generally operate.

The memory 112 can include RAM, ROM, one or more hard drives, one or more flash drives or some other suitable data storage elements such as disk drives, etc. The memory 112 is used to store an operating system and programs, for example. For instance, the operating system provides various basic operational processes for the processor. The programs include various user programs so that a user can interact with the processor 110 to perform various functions such as, but not limited to, viewing and/or manipulating CT images, registration mapping, thresholding, and edge proximity calculations. The CT images can be volumetric CT images.

In some embodiments, the memory 112 can store the volumetric CT images 114 and information related to pose trackable surface sampling tools, such as the shape or geometry of tracer tips of pose trackable tracing tools and known locations within a capture region of intraoral scanners. In other embodiments, the information related to the shape and dimension of the pose trackable surface sampling tool 130 is used in the mathematical operations performed by processor 110, but is not explicitly or separately stored in memory 112. For example, if the pose trackable surface sampling tool 130 has a spherically shaped tip with a radius R for contacting the jaw surface, the calculations performed by processor 110 may be formulated based on that knowledge without the need to explicitly store in memory 112 the tip shape and radius.

In some embodiments, the processor 110 and the memory 112 can be the processor and memory of a computing device (not shown), such as an electronic tablet device, a personal computer, workstation, server, portable computer, mobile device, personal digital assistant, laptop, smart phone, and portable electronic devices or any combination of these.

The communication component may be any interface that enables the dental navigation system 100 to communicate with other devices and systems. In some embodiments, the communication component can include at least one of a serial port, a parallel port or a USB port. The communication component may also include at least one of an Internet, Local Area Network (LAN), Ethernet, Firewire, modem, fiber, or digital subscriber line connection. Various combinations of these elements may be incorporated within the communication component.

For example, the communication component may receive input from various input devices, such as a mouse, a keyboard, a touch screen, a thumbwheel, a track-pad, a track-ball, a card-reader, voice recognition software and the like depending on the requirements and implementation of the dental navigation system 100.

The pose tracker 120 can be a pose tracking system that can track the pose of a pose trackable jaw marker 122 at a sufficiently high accuracy and sufficiently low latency for the targeted application of the system. In some embodiments, the pose tracker 120 can be an optical pose tracking device, for example, the MicronTracker™ by ClaroNav™ Inc. and the pose trackable jaw marker 122 can include an optically trackable jaw tag. In other embodiments, a magnetic tracking system may be used and marker 122 may contain a magnetic field sensing coil.

The pose trackable jaw marker 122 can be attached to the jaw of the patient in a manner that ensures a rigid coupling between the tracked markings on the tag and the jaw to be tracked. For example, the pose trackable jaw marker 122 may be attached to the jaw surface or mounted on the patient's head and held in place at least partially by being pressed against the nasion (i.e., nose bridge) of the patient. The term "jaw surface" relates to any location on the jawbone or any hard or firm object fixated to it (such as teeth, artificial crowns, gums, implants, abutments, or orthodontic hardware). When the pose trackable jaw marker 122 is rigidly coupled to the jaw, an RCS associated with the tag can be used as the jaw RCS. That is, the RCS associated with the tag can be indicative of the jaw RCS.

As shown by the dashed line of FIG. 1, in some embodiments, the dental navigation system 100 also includes a pose trackable surface sampling tool 130 for recording locations along a path traced over a firm surface. The position of the pose trackable surface sampling tool 130 can be tracked by the pose tracker 120 as the pose trackable surface sampling tool 130 traces a path over at least a portion of the surface of the jaw. The pose trackable surface sampling tool 130 can be an intraoral scanner or a pose trackable tracer tool.

The intraoral scanner can be moved over at least one portion of the surface of the jaw without coming into contact with the surface of the jaw. Example intraoral scanners include TRIOS® by 3shape®, CS 3600 by Carestream Dental®, and CEREC OmniCam® by Sirona Dental Systems. Intraoral scanners can have an acquisition pyramid, in which the scanner measures the range from a small camera to the surface in front of the camera. Individual sample points are tiled by triangles to form a continuous surface model of the "patch" being captured by the scanner. In a typical acquisition, the surface patches collected when the scanner tip is moved over the jaw surface are "stitched" together to form a generally continuous surface model. This mechanism can be used to collect dense samples of regions of the jaw surface of arbitrary size.

When the pose trackable surface sampling tool 130 is an intraoral scanner, locations reported by the scanner within its capture region can be mapped to the RCS of the intraoral scanner tracked by pose tracker 120 using the results of a prior calibration process. In such a case, the momentary surface patch captured may be reported to processor 110 in real time, or stitched surface model may be reported to processor 110 in a manner that enables mapping it to the intraoral scanner RCS tracked by pose tracker 120. Intraoral scanners often present a 2-D view of the capture field to their users. A specific location within that view, for example, the view's center, may be marked over the view. The jaw surface location captured at that location can then be mapped to the intraoral scanner RCS, and, subsequently, to the jaw RCS using the pose tracking measurements reported to processor 110 by pose tracker 120.

The pose trackable tracer tool can be moved over at least one portion of the surface of the jaw such that a tracer tip of the pose trackable tracer tool can be in contact with the surface of the jaw. When the shape of the tracer tip is known, the location of the pose trackable surface sampling tool 130 that is recorded by the pose tracker 120 relates to a particular section of the tracer tip. For example, when the tracer tip has a spherical shape, the location of the pose trackable surface sampling tool 130 (i.e., the tracer tip location) can relate to the center of the spherical section of the tracer tip. When the tracer tip has a tapered conic shape, the apex of the cone can be recorded and assumed to be the contact point with the tip surface. More generally, some location on the tracer tool with a known position in the pose trackable tracer RCS can be marked for contact with the jaw surface, then measured and recorded to collect jaw surface samples.

Calibration of a location within the capture region of the intraoral scanner or the tracer tip location can be performed at any time prior to the start of a registration of a human jaw with a volumetric CT image 114 of that jaw positioned in an image RCS.

Figure 2:
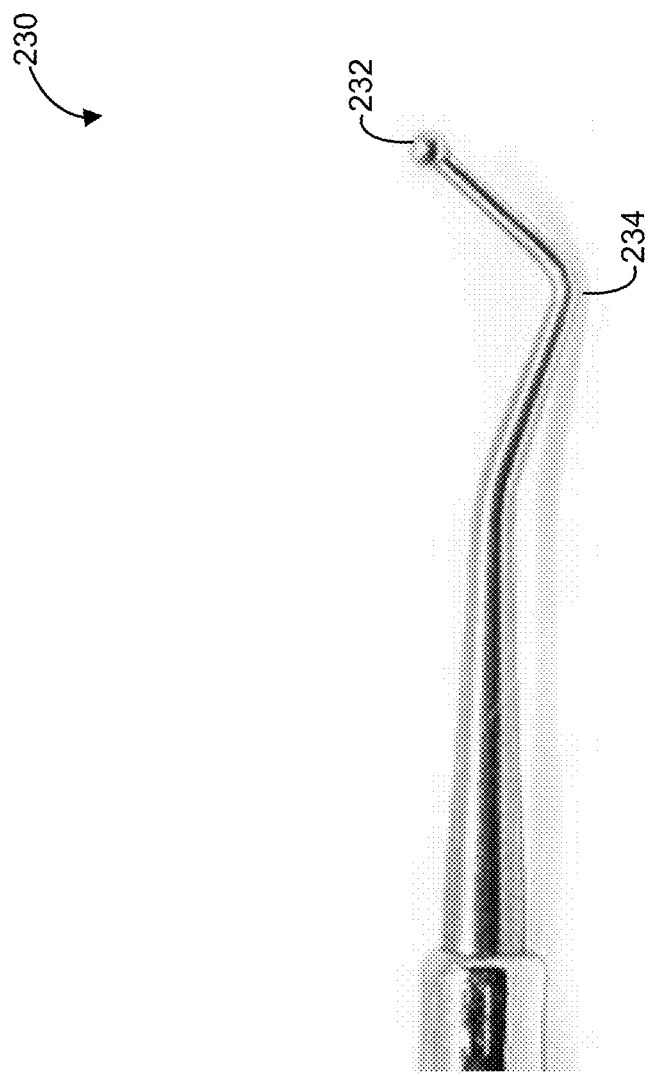
FIG. 2 is an example of a sphere-shaped tip of a position-tracked tool.

Referring now to FIG. 2, shown therein is a portion of an example pose trackable tracer tool 230. The pose trackable tracer tool 230 includes a tracer tip 232. As shown in FIG. 2, the tracer tip 232 of the pose trackable tracer tool 230 can be sphere-shaped. The sphere-shaped tracer tip 232 can have a radius in the range of between about 0.5 millimeters to about 1.0 millimeters. In some embodiments, the radius can be about 0.75 millimeters.

The tracer tip 232 can be mounted on a bent stem 234, similar to dental burnisher tool. In other embodiments, the tracer tip 232 can be a conic (needle) tracer tip (not shown), which is essentially a sphere-shaped tracer tip with a radius close to 0 millimeters. However, conic tips can be less convenient to use in practice because maintaining contact with the surfaces of teeth facing in different directions requires rolling the tracer tip back and forth. Meanwhile, a sphere-shaped tracer tip can be kept in approximately the same orientation while touching a wide range of surface orientations with different sides of the sphere. Furthermore, a sharp tip may cause unnecessary pain to the patient when the tip inadvertently contacts the patient's gums.

Figure 3:
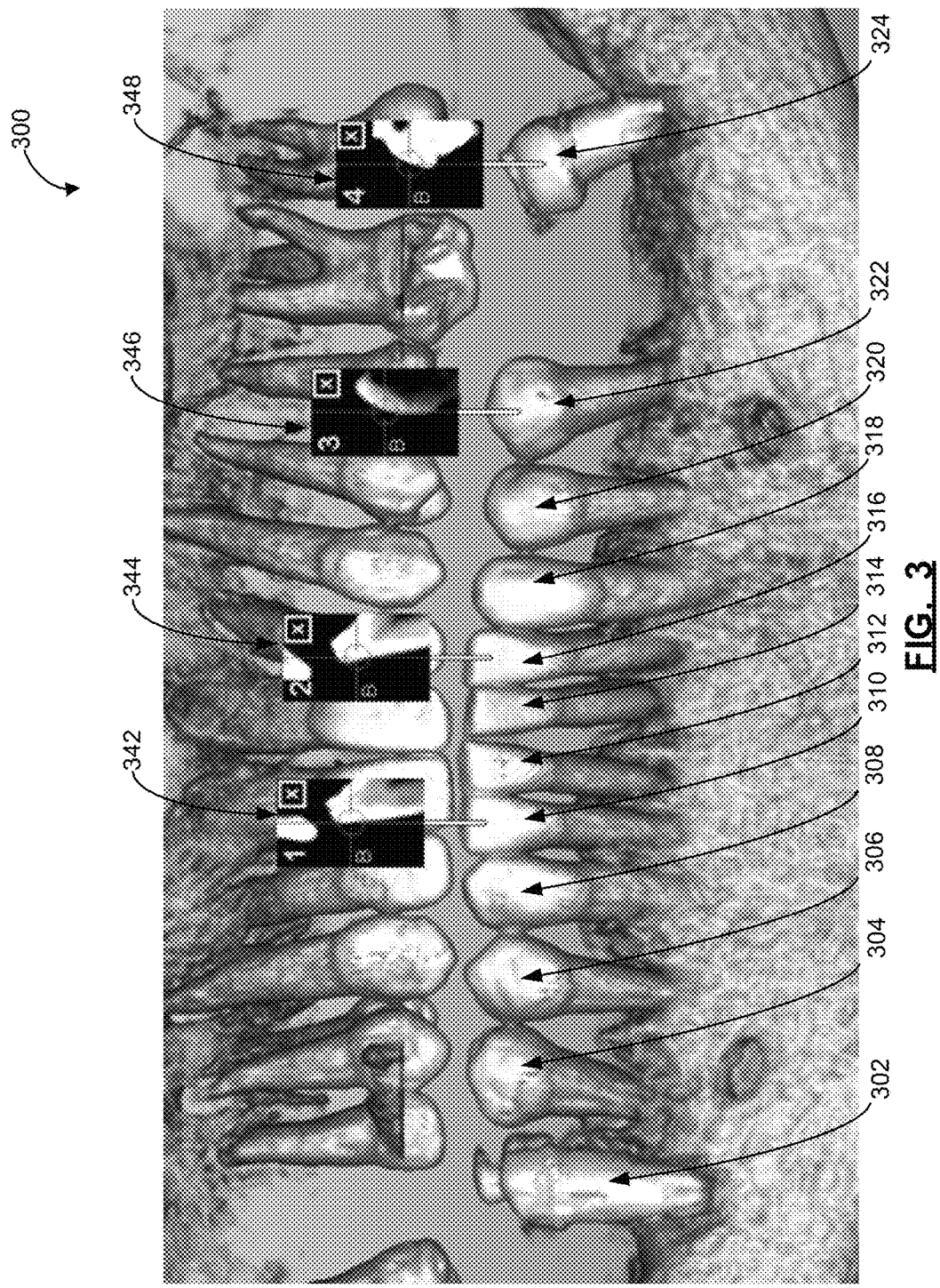
FIG. 3 is an example screen shot of a volumetric computed tomography image of a human jaw.

Referring now to FIG. 3, shown therein is a view image 300 of a volumetric CT image 114 of a human jaw. The volumetric CT image 114 can be stored in memory 110 and displayed in a graphical user interface (GUI) at a computing device (not shown). The view image 300 can show a 3D rendering of the appearance of the jaw surface. In some embodiments, the rendering 300 of the jaw surface can be a projection of a mathematically flattened anatomy along a centerline, or ridge curve of the jaw, a format known in dentistry as panoramic. In some embodiments, the view 300 of the jaw surface can be surface projections from the front, left, and right of the jaw. As shown in FIG. 3, the rendering 300 is a panoramic volumetric rendering of the jaw from the buccal side of the jaw, depicting the surface of the two jaws.

As shown in FIG. 3, 2D rendering 300 can show separate identifiable structures 302, 304, 306, 308, 310, 312, 314, 316, 318, 320, 322, and 324 of the jaw in the image RCS. For example, a separate identifiable structure can be a tooth or an object in rigid geometrical relationship to the jaw such as artificial crowns, implants, abutments, or orthodontic hardware. "Landmark" locations can often be selected on the surfaces of such structures. The term "landmark" is used herein to relate to a location on the jaw surface that can be identified by a user, to within a deviation of less than about 5 millimeters, in both the jaw RCS and in the image RCS.

While being presented with one or more views 300 of the volumetric CT image 114 depicting the surface of the jaw, a user can use a communication component, such as a mouse or touchpad, to move a cursor over the jaw surface shown in the image. To be able to see the location of the cursor in the "depth" direction as well, its location on a reformatted buccal-lingual cross-section image is shown in a small window 342, 344, 346, and 348 near the cursor.

To select and define one or more landmark locations that would be easy to identify later on the actual jaw, the user can point to and click on the one or more landmarks on the jaw surface in the 2D rendering 300 of the volumetric CT image 114. Preferably, the user can define landmarks that are spaced as far apart along the jaw as possible. As the user clicks on a landmark, a cross-section window 342, 344, 346, and 348 can be fixated in place above the selected landmark with a line showing the landmark on the surface. By selecting a landmark, the user can define the landmark and the location of the landmark in image RCS can be recorded in the memory 112.

One or more landmarks can be selected and stored as a sequence. When a plurality of landmarks are selected, the plurality of selected landmarks can be stored as an indexed sequence. In some embodiments, the processor 110 can automatically index the plurality of selected landmarks. As shown in FIG. 3, a user has selected landmarks on three teeth 310, 314, 322, and an implant 324 to be stored as landmarks having indices 1, 2, 3, and 4 as shown in cross-section windows 342, 344, 346, and 348, respectively. In some embodiments, a user may decide to limit the number of landmarks to one, two, or three, or to define additional landmarks beyond four.

Figure 4A:
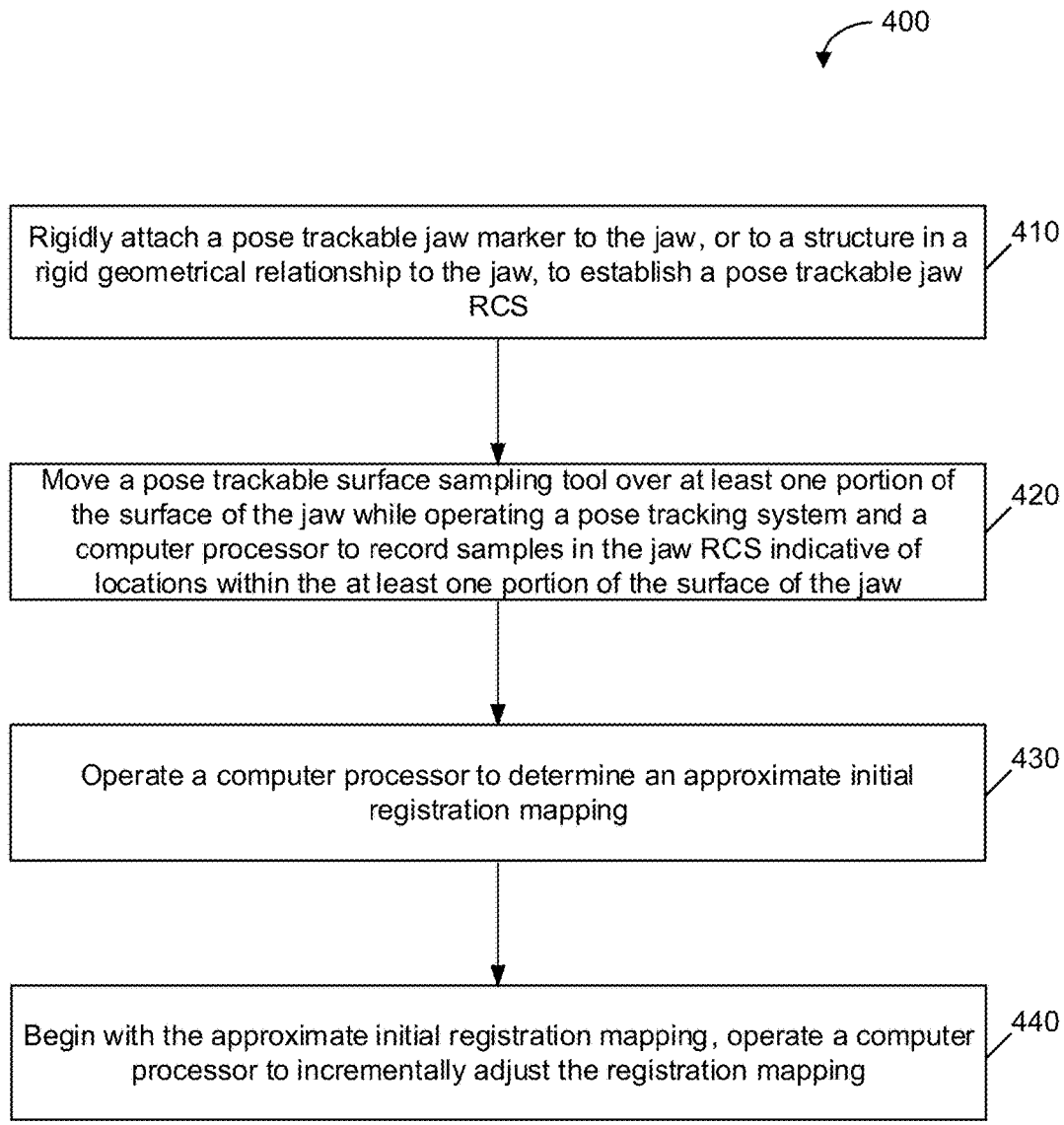
FIGS. 4A and 4B are flowcharts of an example method for registering a human jaw with a volumetric computed tomography image of that jaw positioned in an image reference coordinate system.
Figure 4B:
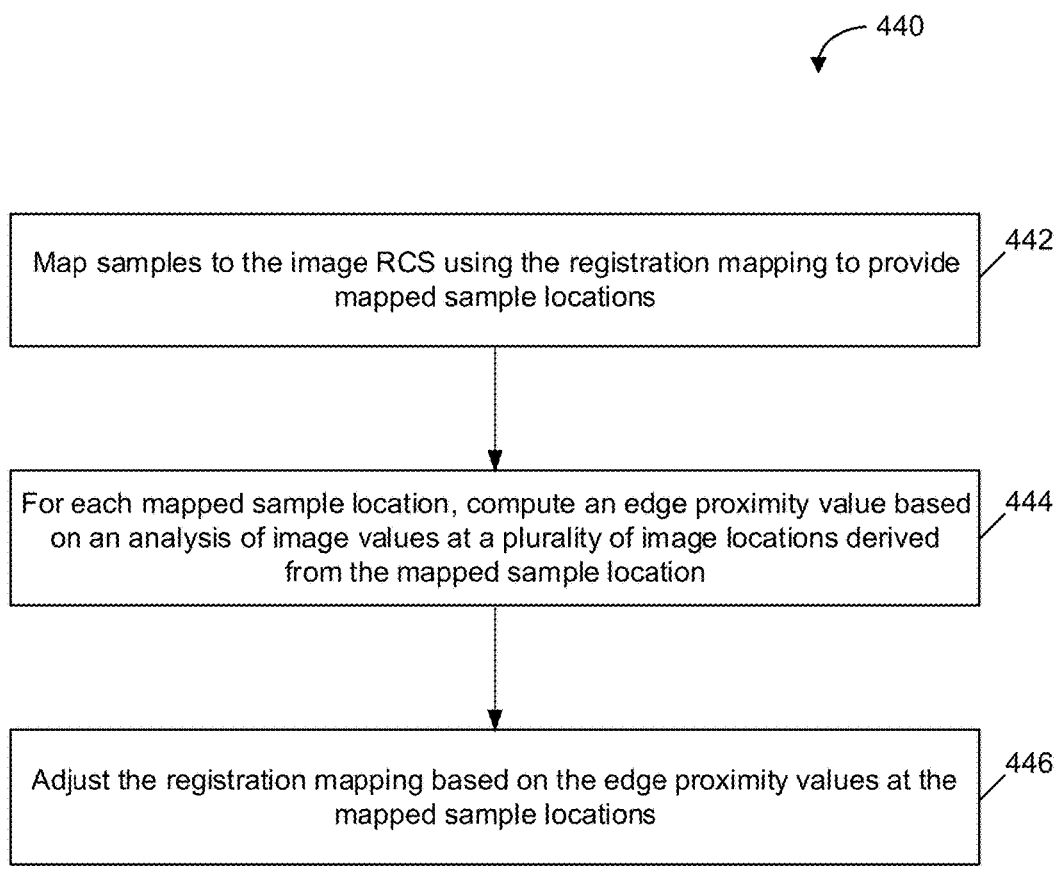

Referring now to FIGS. 4A and 4B, an example method 400 for registering a human jaw with a volumetric computed tomography image of that jaw positioned in an image reference coordinate system is shown in a flowchart diagram. To assist with the description of the method 400, reference will be made simultaneously to FIGS. 3, 5A to 5D, 6, and 7.

At 410, a pose trackable jaw marker 122 is rigidly attached to the jaw, or to a structure in a rigid geometrical relationship to the jaw, to establish a pose trackable jaw RCS. The pose trackable jaw marker 122 can be rigidly attached to the jaw any time prior to 420.

At 420, a pose trackable surface sampling tool 130 is moved over at least one portion of the surface of the jaw while operating a pose tracker 120 and a processor 110 to record samples in the jaw RCS indicative of locations within the at least one portion of the surface of the jaw. The pose trackable surface sampling tool 130 can be moved over the at least one portion of the surface of the jaw in accordance with instructions from the processor 110. More specifically, the processor 110 can display, to the user, a first landmark in a sequence of stored landmarks. The first landmark can be displayed on the 2D rendering 300 of the volumetric CT image 114. The processor 110 can instruct the user to place the pose trackable surface sampling tool 130 on a location on the actual jaw that is homologous, or corresponds, to the landmark location.

Having instructed the user to place the pose trackable surface sampling tool 130 on a homologous location on the actual jaw, the pose tracker 120 can wait to detect that the pose trackable surface sampling tool 130 is in a static position for some threshold time period. Preferably, a static position is indicated by the pose trackable surface sampling tool 130 remaining in the same general position for about 2-3 seconds. Upon detecting that the pose trackable surface sampling tool 130 is in a static position, the pose tracker 120 can record the location of the pose trackable surface sampling tool 130. Alternatively, the user may explicitly signal to processor 110 to record a landmark location by manipulating a switch, such as a foot pedal, or providing a voice command recognizable by a speech recognition program. The user can then be provided with feedback signals to begin tracing the jaw surface in the vicinity of the landmark. In some embodiments, the feedback signal to begin tracing the jaw surface can be a visual signal. Preferably, the feedback signal is an audible signal so that the user can receive the signal without looking at the display.

To trace the jaw surface in the vicinity of a landmark, the user can move the pose trackable surface sampling tool 130 along a path on the jaw surface in the vicinity of the landmark. As the pose trackable surface sampling tool 130 moves along the path, the pose tracker 120 can collect or record landmark trace samples of the location in the jaw RCS of the pose trackable surface sampling tool 130 and the processor 110 can store the landmark trace samples. The term "landmark trace samples" relates to a sequence of locations of the pose trackable surface sampling tool 130, in the Jaw RCS, recorded by the pose tracker 120 while the user traces a path, using the pose trackable surface sampling tool 130, over a region of the jaw surface near a landmark.

In some embodiments, the pose tracker 120 can provide the user with feedback signals during tracing to indicate that the landmark trace samples are being recorded.

Again, the feedback signal is preferably an audible signal so that the user can receive the signal without looking at the display.

The path traced along the jaw surface can traverse multiple teeth, gum surface, and/or structures other than teeth, such as bone surface after gums have been raised to expose the bone surface. Generally, the jaw surfaces being traversed appear as strong edges in the CT image, as illustrated by cross-sections 342, 344, 346, 348.

As the jaw surface is traced, the pose tracker 120 can determine the total distance traveled by the pose trackable surface sampling tool 130 since the homologous location was initially detected. In some embodiments, the pose tracker 120 can compare the total distance traveled with a threshold for a minimum trace distance. When the pose tracker 120 determines that the total distance traveled exceeds the threshold for the minimum trace distance, the pose tracker 120 can stop recording landmark trace samples and/or provide the user with feedback signals to indicate that the total distance traveled is sufficient. In some embodiments, the pose tracker 120 can provide feedback signal to indicate that the total distance traveled is sufficient and then wait to detect that the pose trackable surface sampling tool 130 is in a static position before terminating the recordal of landmark trace samples. In some embodiments, the pose tracker 120 can stop recoding landmark trace samples irrespective of the movement of the pose trackable surface sampling tool 130.

The threshold for the minimum trace distance can have any appropriate value. For example, the minimum trace distance can be approximately 10 centimeters. In some embodiments, the threshold for the minimum trace distance can the same for all landmarks. In some embodiments, the minimum trace distance can be landmark specific and defined when the landmark is defined.

If additional landmarks are defined, the processor 110 can instruct the user to trace the jaw surface in the vicinity of each additional landmark. That is, the processor 110 may iterate through each landmark of the sequence of stored landmarks based on their indexing order. For each landmark, the processor 110 can display that landmark on the 2D rendering 300 of the CT image 114, instruct the user to place the pose trackable surface sampling tool 130 on a location on the actual jaw that is homologous to that landmark location and record the location of the pose trackable surface sampling tool 130, and instruct the user to trace the jaw surface in the vicinity of that landmark and record locations of the pose trackable surface sampling tool 130 as it is moved.

In some embodiments, each landmark relates to different portions of the surface of the jaw. The tracing of the jaw surface in the vicinity of a landmark generates a subset of landmark trace samples for that landmark, that is, the landmark trace. For example, three landmarks can results in three subsets of landmark trace samples.

In some embodiments, if more than one landmark is defined, the pose tracker 120 can include additional requirements to ensure that the appropriate structure is marked as the homologous location of a corresponding landmark. For example, to reduce the likelihood of a user mistaking a tooth for its neighbor when marking an additional landmark on the jaw surface, the pose tracker 120 may enable the recordal of additional landmarks only when the distances of the location being recorded from previously recorded landmarks are within some tolerance (for example, 3 millimeters) from the corresponding distances in the image RCS.

As noted above, when the pose trackable surface sampling tool 130 is an intraoral scanner, the location of the pose trackable surface sampling tool 130 that is recorded by the pose tracker 120 can relate to a marked location in the dynamic capture region image shown to the user of the intraoral scanner. Thus, marking a homologous location of a corresponding landmark on the jaw surface involves positioning the intraoral scanner such that a known location within a capture region of the intraoral scanner corresponds approximately to a landmark location marked on the image 114 and the landmark trace sample can be obtained at the known location within the capture region of the intraoral scanner.

As noted above, when the pose trackable surface sampling tool 130 is a pose trackable tracer tool, the location of the pose trackable surface sampling tool 130 that is recorded by the pose tracker 120 can relate to a tracer tip location that contacts the surface of the jaw. Thus, a homologous location of a corresponding landmark on the jaw surface can involve placing the tracer tip in contact with a location corresponding to a landmark location marked on the image.

As described above, the processor 110 can record landmark trace samples after detecting that the pose trackable surface sampling tool 130 is in a static position, that is, after the landmark is marked, or identified in the jaw RCS. In some embodiments, the processor 110 can record landmark trace samples prior to the identification of the landmark in the jaw RCS. That is, the landmark can be identified in the jaw RCS after the jaw surface in the vicinity of the landmark is traced. The user can move the pose trackable surface sampling tool 130 along a path on the jaw surface in the vicinity of the landmark and then remain in a static position to indicate the landmark location.

When all landmarks and trace samples are collected, the method 400 proceeds to 430 to begin the registration.

At 430, the processor 110 is operated to determine an approximate initial registration mapping. In some embodiments, the processor 110 can compute an initial approximate rigid registration mapping between the jaw RCS and image RCS by aligning the landmark locations marked in the image RCS with the jaw RCS locations of each landmark trace. As noted above, the landmark location can be at the start of a landmark trace, or at the end of a landmark trace.

When the processor 110 is operated to determine an approximate initial registration mapping with less than three landmarks, the three parameters for 3D rotation of the mapping can be estimated based on a known orientation of the jaw relative to the pose trackable jaw marker 122. The processor 110 can be operated to compute the approximate initial registration mapping based on an initial rotation mapping and the at least one corresponding location.

In some embodiments, the orientation of the jaw relative to the pose trackable jaw marker 122 is known from the manner in which the pose trackable jaw marker 122 is attached. For example, when a pose trackable jaw marker 122 is mounted on the patient's head, the orientation of the pose trackable jaw marker 122 relative to the jaw is known. In some embodiments, a tracking camera can be used to detect the location of facial features, such as eyes and mouth, relative to the pose trackable jaw marker 122. The location of facial features relative to the pose trackable jaw marker 122 can then be used to estimate the jaw orientation relative to the pose trackable jaw marker 122. The orientation of the jaw in the image RCS is known from the scanning parameters in the image header. The three parameters for 3D rotation of the approximate initial registration mapping can be estimated by aligning three anatomical axes (e.g., left, anterior, feet) of the jaw in both the jaw RCS and the image RCS.

Having determined the three parameters for 3D rotation, the three parameters for 3D translation can also be estimated. In particular, the three parameters for 3D translation can be estimated from a shift, or difference, between the location of the one landmark in the image RCS and the jaw RCS, or an average of the differences between the locations of the two landmarks in the image RCS and the jaw RCS. Thus, an approximate registration mapping can be determined with less than three landmarks. More specifically, an approximate initial registration mapping can be determined with a single landmark.

While an approximate initial registration mapping can be determined with a single landmark, marking additional landmarks is often desirable. Generally, the initial orientation cannot be estimated accurately enough. As well, there is a need to ensure that tracing traverses multiple jaw surface regions that are spread apart to increase the reliability or accuracy of the final registration mapping. Having more than three landmarks that are spread apart can enable the detection of relative movement between structures from the time that the CT image 114 was taken. However, increasing the number of landmarks also increases the marking and tracing time. As well, a patient may not have a sufficient number of valid structures to be marked.

When the processor 110 is operated to determine an approximate initial registration mapping with three or more landmarks, point-to-point landmark registration can be performed using existing methods, such as Horn's algorithm (Berthold K. P. Horn, Closed-form solution of absolute orientation using unit quaternions", Journal of the Optical Society of America A, Vol 4, pp 629-642, April 1987.). In particular, point-to-point registration can be performed between the locations of the pose trackable surface sampling tool 130 recorded as the homologous landmark locations in the jaw RCS and the landmark locations in the image RCS.

When the pose trackable surface sampling tool 130 is a pose trackable tracer tool, the location in the image RCS to which tip samples are registered can be shifted to account for the shape of the tracer tip. For example, when the tracer tip is spherically shaped and the tip sample locations are recorded at the sphere's center, the landmark marked by the user in image RCS is shifted by the radius of the tip in a direction opposite the image gradient at the landmark (towards the darker side of the edge) to better correspond with the location of the tip sample when the tip was placed in contact with the landmark in the jaw RCS.

At 440, the processor 110 is operated to incrementally adjust the registration mapping, beginning with the approximate initial registration mapping of 430. The approximate initial registration mapping of 430 can be refined to improve the registration accuracy of the rigid registration mapping. The registration mapping can be incrementally adjusted by iteratively adjusting the six degrees of freedom of the mapping, that is, the six control parameters (i.e., three parameters for rotation and three parameters for translation). The registration mapping can be adjusted in 440 based on edge proximity (EP) value returned by an edge proximity function (EPF) over all the landmark trace samples collected.

Referring now to FIG. 4B, shown therein is a flowchart diagram of the method 440 for incrementally adjusting the registration mapping.

At 442, the processor 110 is operated to map the landmark trace samples to the image RCS using the registration mapping to provide mapped sample locations.

At 444, the processor 110 is operated to, for each mapped sample location, compute an edge proximity value based on an analysis of image values at a plurality of image locations derived from the mapped sample location.

At 446, the processor 110 is operated to adjust the registration mapping based on the edge proximity values at the mapped sample locations.

The analysis of image values at a plurality of image locations at 444 from the mapped landmark trace samples can relate to computing an edge proximity function. In some embodiments, computing the edge proximity value can involve image gradients at the plurality of image locations.

The edge proximity function receives, as inputs, a volumetric CT image 114 and a set of landmark trace samples in the image RCS, and determines a scalar EP value. In some embodiments when the pose trackable surface sampling tool 130 is a pose trackable tracer tool, edge proximity function also receives, as an input, measurements based on (or a representation of) the known shape of the tracer tip relative to the landmark trace samples in the image RCS, that is, the distance of the tracer tip sample location to the mapped surface.

The edge proximity function relates to an EP value that increases when, for each sample point, holding the other sample points constant: (a) the surface of the tracer tip of a pose trackable tracer tool or the known location within the capture region of an intraoral scanner, mapped from jaw RCS to the image RCS using the registration mapping, gets closer to a strong edge region in the volumetric CT image 114, and (b) when the magnitude of that strong edge region increases.

The magnitude of the EP value increases when the surface of the tracer tip of the pose trackable tracer tool or the capture region of the intraoral scanner around each landmark trace sample get, on balance, closer to nearby edges of the jaw surface in the volumetric CT image 114 and when the magnitude of these nearby edges of the jaw surface in the volumetric CT image 114, on balance, increases. Thus, at 446, the registration mapping can be adjusted to maximize the EP value.

Various EPF formulations can be used. FIGS. 5A, 5B, 5C, and 5D are schematics illustrating an example formulation of an edge proximity function, in accordance with at least one embodiment. It should be noted that for simplicity, the illustrations 500a, 500b, 500c, and 500d depict in two-dimensional computations. However, the EPF disclosed herein involve three-dimensional computations.

Figures 5A, 5B:
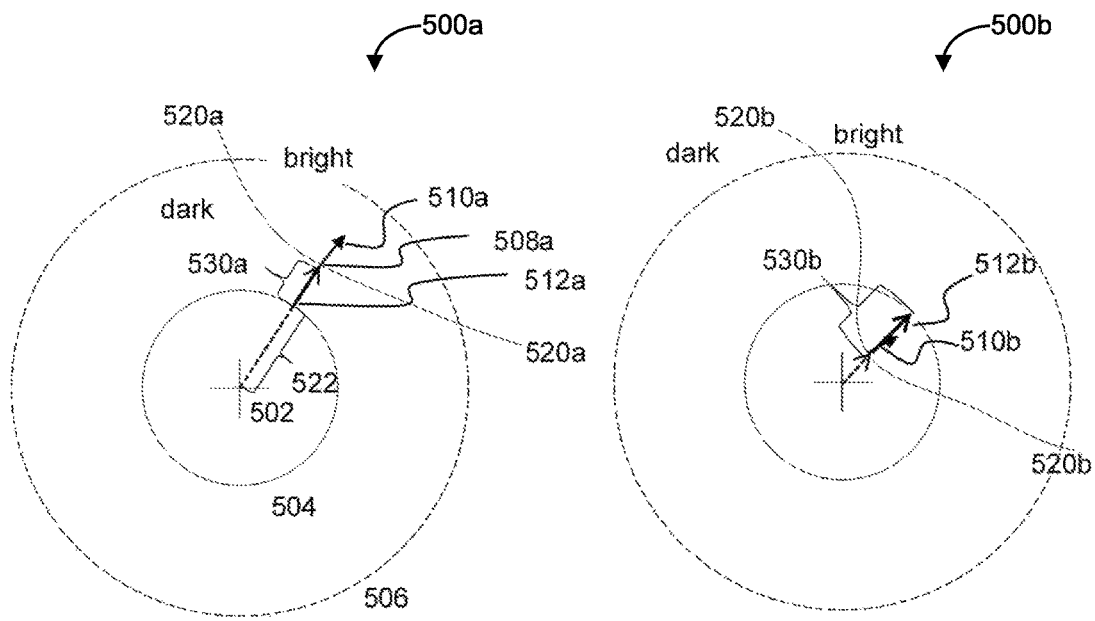
FIGS. 5A, 5B, 5C, and 5D are schematics illustrating an example formulation of an edge proximity function, in accordance with at least one embodiment.

FIG. 5A illustrates an example 500*a* of an EPF having a neighborhood 506 including a search radius (SR) around the surface of the tracer tip 504 and a landmark trace sample point (t$_i$) 502. For example, when the tip of the tracer tool is sphere-shaped, the surface of the tracer tip 504 can be represented by a circle having a radius 522 and the landmark trace sample point 502 can be located at the center of the surface of the tracer tip 504.

Thresholding can be applied to the image region within the neighborhood 506 to separate the image region into bright and dark regions. In CT images, darker regions represent lower density. Any appropriate thresholding can be used. For example, Otsu thresholding can define a boundary surface 520 separating image voxels within the neighborhood 506 as being below and above the threshold. Many other methods are known for segmenting small CT image regions into bright and dark sub-regions. For example, existing segmentation methods in which considerations of gradient magnitude and the smoothness of the dividing surface can be used to improve accuracy when availability of computation resources or time allows.

Having defined the boundary surface 520, a point on the surface 520 that is closest to a landmark trace sample point (t$_i$) 502 can be selected as surface point (s$_i$) 508. As shown in FIG. 5A, surface point (s$_i$) 508*a* has a distance 522 from the trace sample point (t$_i$) 502 in the direction indicated by vector 512*a*, namely (t$_i$−s$_i$). The surface point (s$_i$) 508*a* has an image gradient 510*a*.

In some embodiments, the EPF can be defined as a sum over all trace samples, as in Equation (1):

$$EPF = \sum \frac{g(s_i)}{d(t_i, s_i) + C} \quad (1)$$

where g(s$_i$) is the image gradient magnitude at
d(t$_i$,s$_i$) is a contact distance function; and
C is a constant.

The constant, C, can be empirically selected to prevent the value derived for each same from rising too high when the contact distance is near 0. For example, C can be 0.5.

The contact distance function d(t$_i$,s$_i$), can represent the estimated distance 530*a* that the tracer tip of the tracer tool mapped to image RCS (t$_i$) 502 needs to be translated in order for the surface of the tracer tip 504 to be in proper contact with the surface point (s$_i$) 508.

As shown in Equation (1), the EPF can be the summation of the ratio of the image gradient magnitude and the contact distance function. In other embodiments, the EPF can be the average of the ratio of the image gradient magnitude and the contact distance function.

Since the pose trackable surface sampling tool 130 is expected to be outside of the high-density structure being traced at the point of contact between the tracer tip and the surface of the structure, the image gradient 510*a* is expected to be approximately aligned with the surface normal of the tracer tip 530*a*. That is, the image gradient 510 is expected to be pointing radially away from the center of the tracer tip 504. Mathematically, the alignment of the image gradient 510*a* with the surface normal of the tracer tip 530*a* is indicated by the sign of the dot product between image gradient 510*a* and the vector 512*a*.

FIGS. 5A and 5B illustrate examples 500*a*, 500*b* where the sign of the dot product between image gradient 510*a*, 510*b* and the vector 512*a*, 512*b* is positive, and the contact distance 530*a*, 530*b* can be computed as follows in Equation (2):

$$d(t_i,s_i)=|(\|t_i-s_i\|-TR)| \quad (2)$$

where TR is radius of a sphere-shaped tracer tip of a pose trackable tracer tool.

Figures 5C, 5D:
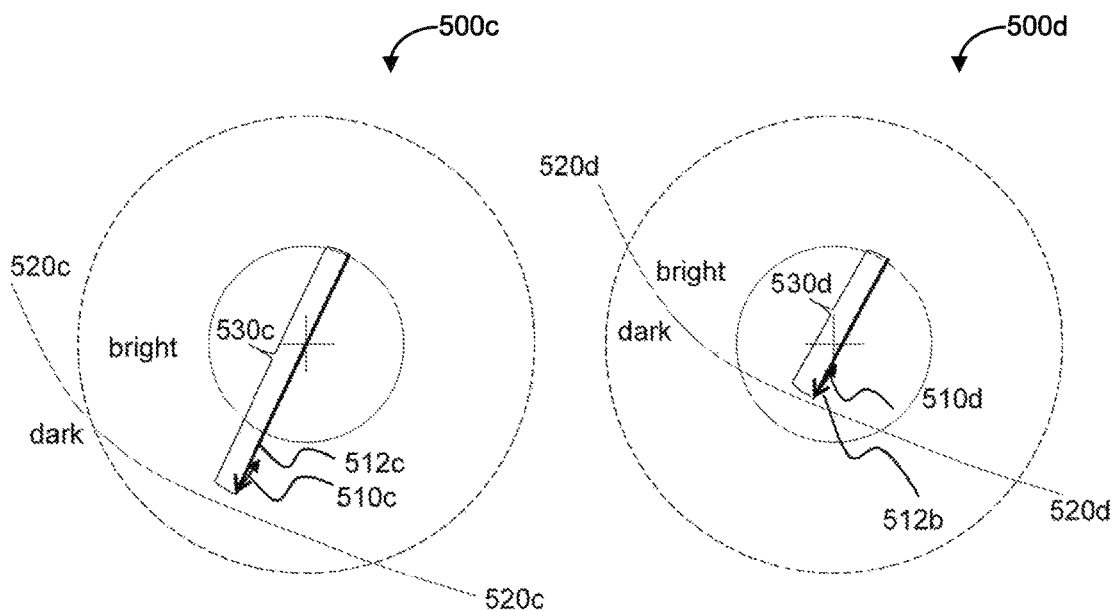

FIGS. 5C and 5D illustrate examples 500*c*, 500*d* where the signs of the dot products between image gradients 510*c*, 510*d* and the vectors 512*c*, 512*d* are negative, and the contact distances 530*c*, 530*d* can be computed as follows in Equation (3):

$$d(t_i,s_i)=\|t_i-s_i\|+TR \quad (3)$$

Figure 6:
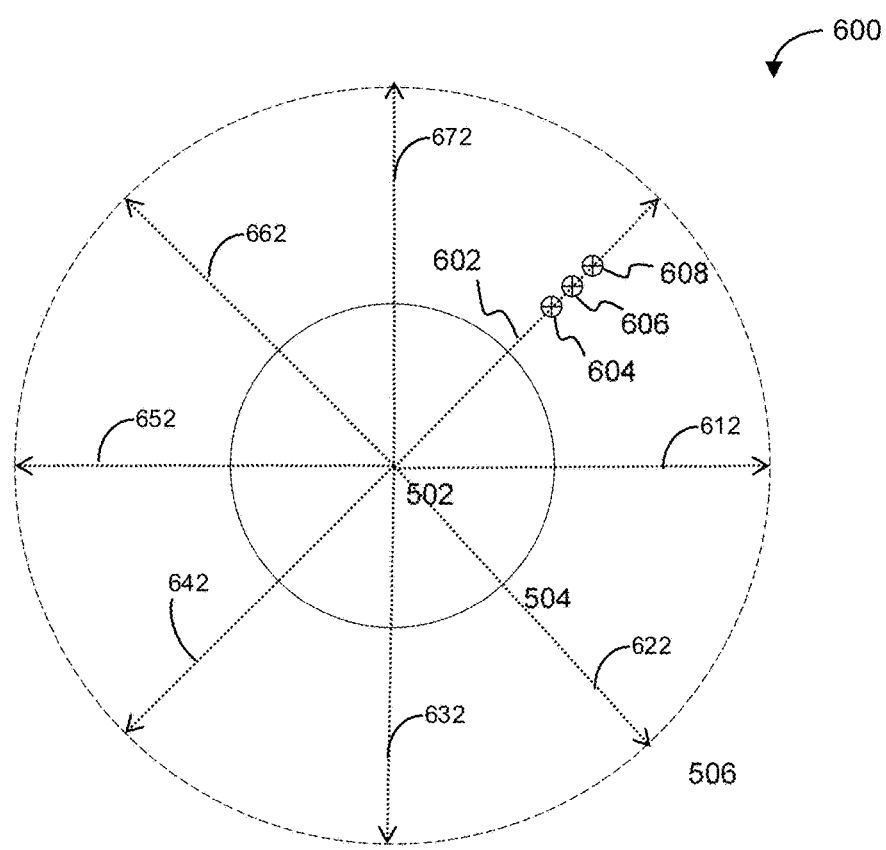
FIG. 6 is a schematic illustrating an example formulation of less precise an edge proximity function, in accordance with at least one embodiment.

FIG. 6 is a schematic illustrating an example 600 of a less precise edge proximity function, in accordance with at least one embodiment. However, the EPF formulation illustrated in FIG. 6 can be advantageous because it is less computationally intensive and thus, more suitable to be used in cases where the computation time using the EPF formulation of FIGS. 5A to 5D is unacceptably long.

Similar to FIGS. 5A to 5D, example 600 illustrates a two-dimensional computation for simplicity. However, the EPF disclosed herein involves three-dimensional computations. In addition, similar to the examples shown in FIGS. 5A to 5D, point 502 relates to landmark sample point t$_i$, and circles 504 and 506 represent the surface of a sphere-shaped tracer tip having radii TR and a search radius SR around the surface of the tracer tip, respectively.

In example 600, virtual "rays" are cast from 502 in various directions, with the image values sampled (using interpolation) at locations along each ray. FIG. 6 illustrates a plane in which eight rays 602, 612, 622, 632, 642, 652, 662, 672 are cast 45 degrees apart. In 3D, a similar ray distribution will result in 26 isotropic rays. A larger or smaller number of rays can be cast to adjust to the available computation power and accuracy required.

At each sample point 606 along ray 602, the value at the previous sample 604 is subtracted from the value at the next sample point 606 to derive an estimate PGM (projected gradient magnitude) of the local gradient projected on ray 602. Surface point s$_i$ is then selected where the absolute value of PGM is the highest, and the contact distance function d(t$_i$,s$_i$), is then computed as described in relation to FIGS. 5A to 5D, with the sign of PGM replacing the sign of the dot product between gradient 510 and the vector 512.

The EPF examples illustrated in FIGS. 5A to 5D and 6 assume a spherical tracer tip. However, other, non-spherical shaped tracer tips and capture regions can be used. In such cases, however, the mapping of the tracer tip to the image RCS needs to include the orientation of the tracer tip, if its shape is not symmetrical, and surfaces of the tracer tip 504 and the search region surfaces 506 need to be modified accordingly.

The optimization iterations in 440 can proceed by repeatedly performing point-to-point registrations between the landmark trace samples in jaw RCS and their corresponding nearest surface points s$_i$ (508*a* in FIG. 5A) in image RCS until the value of EPF peaks, or by other known iterative optimization methods, such as gradient descent or simplex. Multiple optimization methods can be used, sequentially or intermixed.

In some embodiments, when more than three landmarks are used, the system can evaluate the quality of the registration mapping for each landmark trace. The system can adopt a "leave one out" approach to detect cases where a landmark trace was not properly performed or where the tooth being traced has moved relative to the rest of the jaw between the time the image was taken and the surgery. The system may use the registration mapping without this landmark trace, and/or the system may notify the user to suggest that the landmark be moved to another structure or that the tracing for that landmark be repeated.

To evaluate the quality of the registration mapping for a landmark trace, the system may compute two additional registration mappings for each landmark: (1) starting with the previous (globally optimized) registration mapping, it is further optimized using only the landmark trace samples set to produce a locally optimized mapping, and (2) using the complementary set of landmark trace samples from the other landmarks to produce a complementarily optimized mapping. That is, referring back to FIG. 4B, the processor 110 can perform steps 442, 444, and 446 for (1) a subset of samples, such as a subset of landmark trace samples for a single landmark to determine a trace-specific adjusted registration mapping for that landmark, and (2) for all of the remaining subsets of samples besides that single landmark to determine a complementary adjusted registration mapping.

The processor 110 can determine a difference between the trace-specific adjusted registration mapping and the complementary adjusted registration mapping. More specifically, the average shift (distance) for each landmark trace in the image RCS between the landmark trace samples mapped using the local and using the complementarily optimized mappings can then be computed.

If the shift (distance) is found to be higher than, or exceeds a maximum threshold (for example, 1.0 millimeter), it is likely that either that landmark trace was not properly performed or that the tooth being traced moved relative to the rest of the jaw between the time the image was taken and the surgery. The processor 110 can then use the complementary optimized mapping for this landmark as the registration mapping (i.e., the system may use the registration mapping without the landmark trace), and/or the processor 110 can send a notification or alert to the user identifying the subset of samples that resulted in a trace-specific adjusted registration mapping exceeding the maximum threshold and a suggestion to move that landmark to another structure or to repeat the tracing for that landmark.

Figure 7:
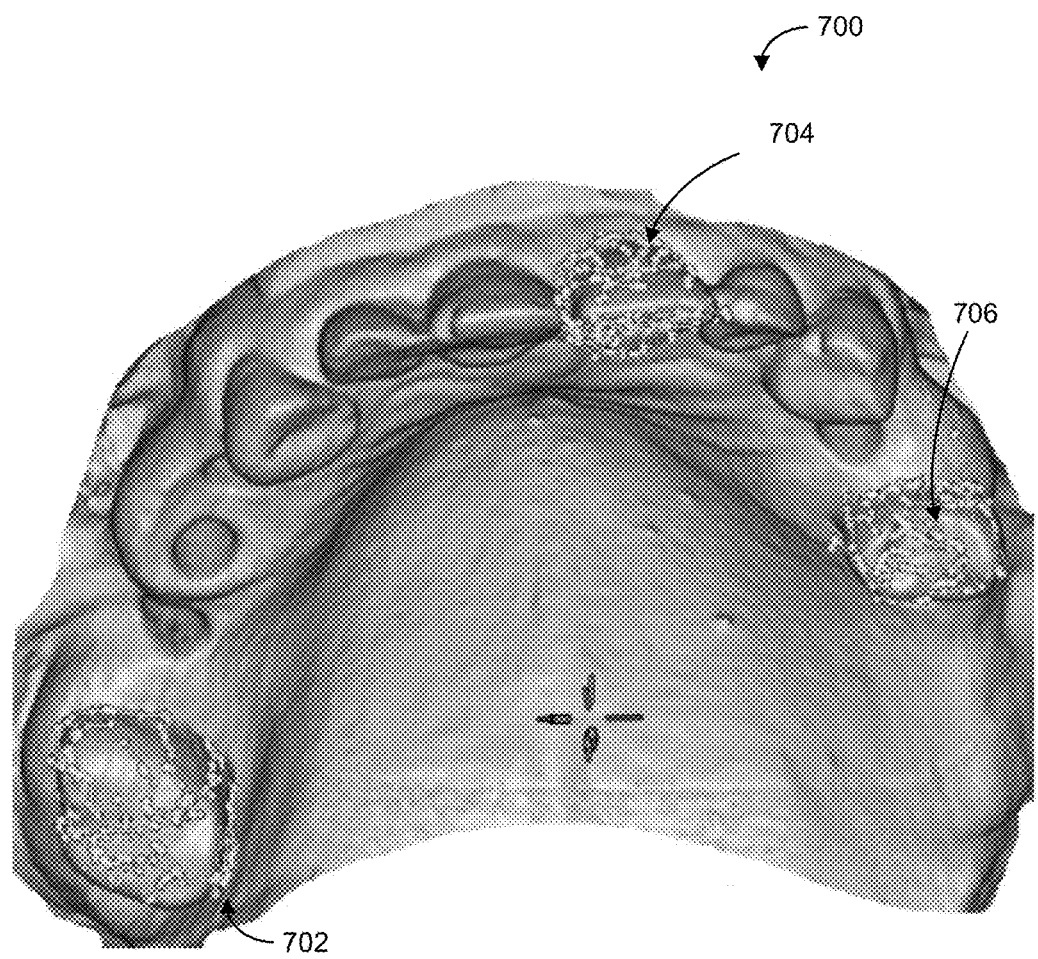
FIG. 7 shows an example of trace samples collected from the surface of three landmarks, mapped to a 3D rendered view of a model jaw using a registration algorithm, in accordance with at least one embodiment.

FIG. 7 shows an example 700 of trace samples collected from the surface of three landmarks, mapped to a 3D rendered view of a model jaw using a registration method, in accordance with at least one embodiment. In particular, about 250 landmark trace samples for each of the three landmarks 702, 704, and 706 are mapped to the model jaw in example 700. The landmark traces samples are shown in FIG. 7 as small spheres. Trace samples mapped in a model jaw, such as example 700, can enable a subsequent, optional quality assessment step.

In another, optional, quality assessment step, the user can check the registration mapping accuracy by bringing the tracer tip of a pose trackable tracer tool into contact with the jaw surface, that is, jaw structures in the jaw RCS and observing whether the location of the tracer tip is correctly shown in the image RCS.

The dental navigation system 100 can map the center of the tracer tip to the image (see e.g., 502 in FIG. 5A), determine the nearest surface point 508 in the image, and render an image reformatted on a plane that includes both the mapped tip 502 and the nearest surface point 508.

To determine the nearest surface point 508, the system 100 can use the same computation as that in the EPF algorithm of 444. That is, the system 100 can use a function to examine the image values in a region surrounding the tracer tip of a pose trackable surface sampling tool 130 mapped through the registration mapping to image RCS to estimate the image edge location that most likely represents the jaw surface location nearest the surface of the tracer tip.

The system 100 can then present to the user an image reformatted along a plane that contains both the tip location and the image edge location. The intersection of that reformatting plane with the tracer tip shape is shown overlaid on the plane, which enables the user to visually assess the registration accuracy at that surface location.

Figure 8:
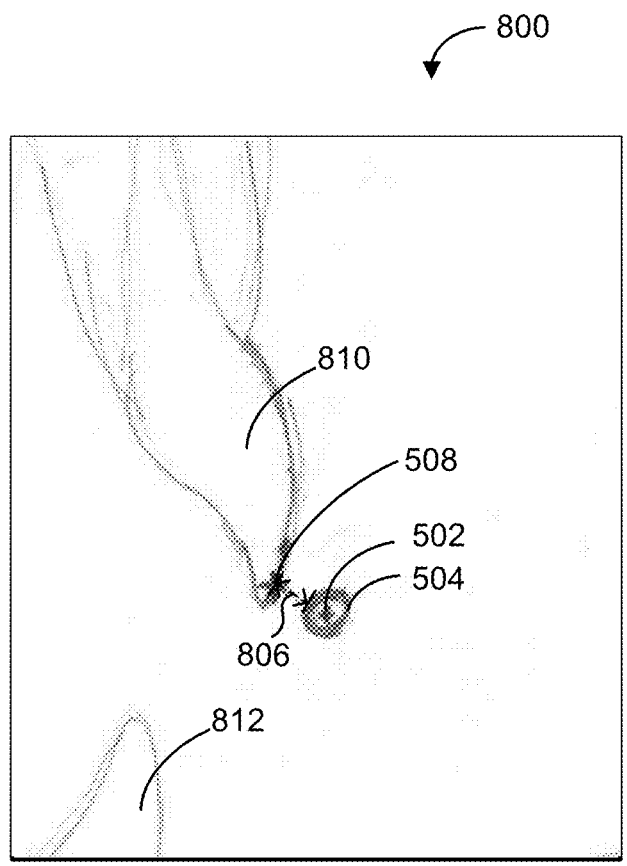
FIG. 8 shows an example image slice for assessing registration accuracy.

Referring now to FIG. 8, shown therein is an example image slice 800 for assessing the registration accuracy. The image slice 800 shows an upper incisor 810 and lower incisor 812 of a human jaw. As shown in FIG. 8, the tracer tip shape is spherical, indicated by a circle 504 overlaid on the image slice, and the tip location 502 is indicated at the center of the circle 504. The image slice 800 also illustrates the inaccuracy gap 806 between the surface of the tracer tip 504 and the image edge location 508 that most likely represents the jaw surface location nearest the surface of the tracer tip.

For ease of user viewing, it is preferable that the reformatting plane be similar to the familiar buccal-lingual view. To achieve the buccal-lingual view, the buccal-lingual view plane passing through the tip's center 502 is first computed, and then the plane is rotated around a head-feet oriented axis going through point 502 to include point 508. This quality assessment step can be iteratively performed for any number of jaw surfaces.

Various embodiments have been described herein by way of example only. Various modification and variations may be made to these example embodiments without departing from the spirit and scope of the invention, which is limited only by the appended claims.

The invention claimed is:

1. A method for registering a human jaw with a volumetric computed tomography image of that jaw positioned in an image reference coordinate system and stored in a computer-readable memory, the method comprising:
   rigidly attaching a pose trackable jaw marker to the jaw, or to a structure in a rigid geometrical relationship to the jaw, to establish a pose trackable jaw reference coordinate system;
   moving a pose trackable surface sampling tool over at least one portion of the surface of the jaw while operating a pose tracking system and a computer processor to record samples in the jaw reference coordinate system indicative of locations within the at least one portion of the surface of the jaw;
   operating a computer processor to determine an approximate initial registration mapping; then
   beginning with the approximate initial registration mapping, operating the computer processor to incrementally adjust the registration mapping by:
   i) mapping the samples to the image reference coordinate system using the registration mapping to provide mapped sample locations,
   ii) for each mapped sample location, computing an edge proximity value based on an analysis of image values at a plurality of image locations derived from the mapped sample location, and
   iii) adjusting the registration mapping based on the edge proximity values at the mapped sample locations.

2. The method as defined in claim 1 wherein computing the edge proximity value comprises computing image gradients at the plurality of image locations.

3. The method as defined in claim 1, wherein computing the edge proximity value comprises:
   analyzing image values at a plurality of image locations derived from the mapped sample location to select an image location; and
   computing a distance from the selected image location to another image location derived from the mapped sample location.

4. The method as defined in claim 1, wherein the pose trackable surface sampling tool comprises an intraoral scanner.

5. The method as defined in claim 4, wherein:
   the method further comprises marking at least one corresponding location in both the image reference coordinate system and the jaw reference coordinate system; and
   determining an approximate initial registration mapping comprises:
      computing an initial rotation mapping based on estimating the orientation of the jaw in the jaw reference coordinate system based on a known orientation of the jaw relative to the jaw marker; and
      computing the initial registration mapping based on the initial rotation mapping and the at least one corresponding location.

6. The method as defined in claim 5, wherein:
   the method further comprises marking on the image at least one landmark location on the jaw surface;
   positioning the intraoral scanner such that a known location within a capture region of the intraoral scanner corresponds approximately to a landmark location marked on the image and obtaining a sample location at the known location within the capture region; and
   determining an approximate initial registration mapping is based at least in part on the correspondence between the at least one landmark location marked on the image and the sample location at the known location within the capture region.

7. The method as defined in claim 6, wherein the landmark location is marked on a rendering of the jaw surface which is mathematically flattened along a ridge curve of the jaw.

8. The method as defined in claim 5, wherein:
   the method further comprises marking on the image at least one landmark location on the jaw surface;
   moving the pose trackable surface sampling tool over at least one portion of the surface of the jaw starts at a location corresponding to a landmark location marked on the image; and
   determining an approximate initial registration mapping is based at least in part on the correspondence between the at least one landmark location marked on the image and a sample location recorded at the start of moving the pose trackable surface sampling tool.

9. The method as defined in claim 5, wherein
   the method further comprises marking on the image at least one landmark location on the jaw surface;
   moving the pose trackable surface sampling tool over at least one portion of the surface of the jaw ends at a location corresponding to a landmark location marked on the image; and
   determining an approximate initial registration mapping is based at least in part on the correspondence between the at least one landmark location marked on the image and a sample location recorded at the end of moving the pose trackable surface sampling tool.

10. The method as defined in claim 1, wherein the pose trackable surface sampling tool is a pose trackable tracer tool with a tracer tip of known shape, and moving a surface sampling tool comprises dragging the tracer tip over at least one portion of the surface of the jaw such that the tracer tip contacts the surface of the jaw.

11. The method as defined in claim 10, further comprising, after determining a final registration, performing a visual registration accuracy check, such accuracy check comprising:
   placing the tracer tip in contact with a jaw surface location;
   mapping the tracer tip to the image reference coordinate system using the registration mapping;
   selecting an image location likely to correspond to the jaw surface location nearest to the mapped tracer tip surface based on analyzing image values at a plurality of image locations derived from the mapped surface of the tracer tip; and
   displaying an image illustrating the gap between the selected image location and the mapped tracer tip surface location closest to the selected image location.

12. The method as defined in claim 10, wherein the tracer tip shape is substantially spherical, and selecting the plurality of image locations in the computation of the edge proximity value in step ii) of adjusting the registration mapping comprises defining a plurality of vectors emanating in different directions from the mapped center of the tracer tip and selecting locations along each such vector.

13. The method as defined in claim 1, wherein moving the pose trackable surface sampling tool over at least one portion of the surface of the jaw comprises moving the pose trackable surface sampling tool over at least three portions of the surface of the jaw such that the samples comprise at least three subsets of samples, each subset of samples being from a different portion of the surface of the jaw in the at least three portions of the surface of the jaw.

14. The method as defined in claim 13, wherein operating the computer processor to incrementally adjust the registration mapping further comprises, for each subset of samples:
   operating the computer processor to perform step i) to step iii) for that subset of samples to adjust the registration mapping to determine a trace-specific adjusted registration mapping;
   operating the computer processor to perform step i) to step iii) for all of the remaining subsets of samples to adjust the registration mapping to determine a complementary adjusted registration mapping; and
   determining a difference between the trace-specific adjusted registration mapping and the complementary adjusted registration mapping, and, when that difference exceeds a maximum threshold, then further operating the computer processor to send a notification identifying that subset of samples.

15. A system for registering a human jaw with a volumetric computed tomography image of that jaw positioned in an image reference coordinate system, the system comprising:
   a pose trackable jaw marker that is rigidly attachable to the jaw or to a structure in a rigid geometrical relationship to the jaw to establish a pose trackable jaw reference coordinate system;
   a pose tracker for tracking poses of the pose trackable jaw marker and a pose trackable surface sampling tool;
   a computer-readable memory for storing the volumetric computed image; and a computer processor operatively coupled to the computer-readable memory and the pose tracker, the computer processor being configured for:
recording samples in the jaw reference coordinate system indicative of locations within the at least one portion of the surface of the jaw while the pose trackable surface sampling tool is moved over at least one portion of the surface of the jaw;
determining an approximate initial registration mapping; then beginning with the approximate initial registration mapping,
incrementally adjusting the registration mapping by:
i) mapping the samples to the image reference coordinate system using the registration mapping to provide mapped sample locations,
ii) for each mapped sample location, computing an edge proximity value based on an analysis of image values at a plurality of image locations derived from the mapped sample location, and
iii) adjusting the registration mapping based on the edge proximity values at the mapped sample locations.

16. The system as defined in claim 15, wherein the computer processor being configured for computing the edge proximity value comprises the computer processor being configured for computing image gradients at the plurality of image locations.

17. The system as defined in claim 15, wherein the computer processor being configured for computing the edge proximity value comprises the computer processor being configured for:
analyzing image values at a plurality of image locations derived from the mapped sample location to select an image location; and
computing a distance from the selected image location to another image location derived from the mapped sample location.

18. The system as defined in claim 15, further comprising the pose trackable surface sampling tool.

19. The system as defined in claim 15, wherein the pose trackable surface sampling tool comprises an intraoral scanner.

20. The system as defined in claim 19, wherein:
the computer processor is further configured for receiving at least one corresponding location in both the image reference coordinate system and jaw reference coordinate system; and
the computer processor being configured for determining an approximate initial registration mapping comprises the computer processor being configured for:
computing an initial rotation mapping based on estimating the orientation of the jaw in the jaw reference coordinate system based on a known orientation of the jaw relative to the jaw marker; and
computing the initial registration mapping based on the initial rotation mapping and the at least one corresponding location.

21. The system as defined in claim 20, wherein the computer processor is further configured for:
receiving at least one landmark location on the jaw surface on the image;
receiving a sample location at a known location within a capture region of the intraoral scanner when the intraoral scanner is positioned with the known location within the capture region at approximately a landmark location marked on the image; and
determining an approximate initial registration mapping based at least in part on the correspondence between the at least one landmark location marked on the image and the sample location at the known location within the capture region.

22. The system as defined in claim 21, wherein the landmark location is marked on a rendering of the jaw surface which is mathematically flattened along a ridge curve of the jaw.

23. The system as defined in claim 20, wherein the computer processor is further configured for:
receiving at least one landmark location on the jaw surface on the image;
receiving a sample location when the pose trackable surface sampling tool starts to be moved over at least one portion of the surface of the jaw at a location corresponding to a landmark location marked on the image; and
determining an approximate initial registration mapping based at least in part on the correspondence between the at least one landmark location marked on the image and a sample location recorded at the start of moving the pose trackable surface sampling tool.

24. The system as defined in claim 20, wherein the computer processor is further configured for:
receiving at least one landmark location on the jaw surface on the image;
receiving a sample location when the pose trackable surface sampling tool stops being moved over at least one portion of the surface of the jaw at a location corresponding to a landmark location marked on the image; and
determining an approximate initial registration mapping based at least in part on the correspondence between the at least one landmark location marked on the image and a sample location recorded at the end of moving the pose trackable surface sampling tool.

25. The system as defined in claim 15, wherein:
the pose trackable surface sampling tool comprises a pose trackable tracer tool with a tracer tip of known shape for contacting the surface of the jaw as the pose trackable surface sampling tool is moved; and
the computer-readable memory further stores the shape of the tracer tip.

26. The system as defined in claim 25, further comprising, the computer processor being configured for after determining a final registration, performing a visual registration accuracy check, such accuracy check comprising:
receiving a tracer tip when the tracer tip is in contact with a jaw surface location;
mapping the tracer tip to the image reference coordinate system using the registration mapping;
selecting an image location likely to correspond to the jaw surface location nearest to the mapped tracer tip surface based on analyzing image values at a plurality of image locations derived from the mapped surface of the tracer tip; and
displaying an image illustrating the gap between the selected image location and the mapped tracer tip surface location closest to the selected image location.

27. The system as defined in claim 25, wherein the shape of the tracer tip is substantially spherical, and the computer processing being configured for selecting the plurality of image locations in the computation of the edge proximity value in step ii) of adjusting the registration mapping comprises the computer processing being configured for defining a plurality of vectors emanating in different directions from the mapped center of the tracer tip and selecting locations along each such vector.

28. The system as defined in claim 15, wherein the computer processor being configured for recording samples in the jaw reference coordinate system indicative of locations within the at least one portion of the surface of the jaw while the pose trackable surface sampling tool is moved over at least one portion of the surface of the jaw comprises the computer processor being configured for recording samples in the jaw reference coordinate system indicative of at least three portions of the surface of the jaw such that the samples comprise at least three subsets of samples, each subset of samples being from a different portion of the surface of the jaw in the at least three portions of the surface of the jaw.

29. The system as defined in claim 28, wherein the computer processor being configured for incrementally adjusting the registration mapping further comprises, for each subset of samples:

performing step i) to step iii) for that subset of samples to adjust the registration mapping to determine a trace-specific adjusted registration mapping;

performing step i) to step iii) for all of the remaining subsets of samples to adjust the registration mapping to determine a complementary adjusted registration mapping; and determining a difference between the trace-specific adjusted registration mapping and the complementary adjusted registration mapping, and, when that difference exceeds a maximum threshold, then further the computer processor being further configured for sending a notification identifying that subset of samples.

* * * * *